United States Patent [19]
Griller et al.

[11] Patent Number: 4,973,783
[45] Date of Patent: Nov. 27, 1990

[54] DEHALOGENATION OF HALOGENATED AROMATIC COMPOUNDS

[75] Inventors: David Griller, Ontario; Jalal A. Hawari, Quebec; Derek J. McPhee, Ontario, all of Canada

[73] Assignee: National Research Council Canada/Conseil national de recherches Canada, Ottawa, Canada

[21] Appl. No.: 324,004

[22] Filed: Mar. 16, 1989

[30] Foreign Application Priority Data

Mar. 18, 1988 [CA] Canada ................................ 561934

[51] Int. Cl.$^5$ ................................................ C07C 1/20
[52] U.S. Cl. .................................. 585/469; 208/262.1; 208/262.5; 588/208; 588/210; 588/249; 588/901
[58] Field of Search .................... 588/1208 H, 1211 Y, 588/1273 T, 1295 D; 885/469; 208/262.1, 262.5

[56] References Cited

U.S. PATENT DOCUMENTS

| 2,377,689 | 6/1945 | Hyde .............................. 106/287.13 |
| 4,012,401 | 3/1977 | Prokai ................................ 502/167 |
| 4,353,793 | 10/1982 | Brunelle ........................... 208/262.5 |
| 4,526,677 | 7/1985 | Grantham et al. ................ 208/262.5 |
| 4,853,040 | 8/1989 | Mazur et al. ....................... 208/179 |

FOREIGN PATENT DOCUMENTS

| 1181771 | 1/1985 | Canada ................................. 585/469 |
| 0118858 | 9/1984 | European Pat. Off. ......... 208/262.1 |
| 52-036650 | 3/1977 | Japan ................................... 585/469 |

OTHER PUBLICATIONS

Introduction to the Chemistry of the Silicones, Rochow (1951), pp. 78–91.
Condensed Chemical Dictionary (9th Ed), Hawley (1980), pp. 774 to 776.

Primary Examiner—Patrick P. Garvin
Assistant Examiner—James A. Saba
Attorney, Agent, or Firm—Alan A. Thomson

[57] ABSTRACT

Various halogenated aromatic compounds, particularly polychlorinated biphenyls, and the like, are dehalogenated by reaction with alkali metal in the presence of liquid hydrosiloxane. A selected solvent or diluent may be present. The alkali metal halide reaction product may be removed by washing. It has been found substantially complete dehalogenation is achieved readily at ambient temperatures when the hydrosiloxane is present. The dehalogenated aromatic moiety normally is recovered intact. This method has been found very effective in the destruction and removal of PCB contaminants.

14 Claims, No Drawings

DEHALOGENATION OF HALOGENATED AROMATIC COMPOUNDS

This invention deals with the removal of halogen atoms from halogenated aromatic materials especially the aromatics based on benzene, biphenyl, other polyphenyls, naphthalene, anthracene and the like. The halogen substituents are reacted with alkali metal in the presence of a hydrosiloxane. The hydrosiloxane has been found to facilitate the reaction so that it will proceed to completion at room temperature in relatively short times.

BACKGROUND AND PRIOR ART

Polychlorinated biphenyls (PCBs) are organic chemicals that were produced on a large scale in the period 1930-1980. Approximately 600,000 tons of the material were manufactured and were used in a wide variety of applications. However, the most important use for the material was as an insulator in electrical transformers and capacitors. PCBs were ideally suited to this role because of their chemical inertness and lack of flammability.

In the mid 1970s concerns began to be expressed about the detrimental effects of PCBs on health and the environments. While these concerns were not substantiated to a large extent, there still existed a very strong public pressure to eliminate the use of PCBs. Accordingly, large scale manufacture was halted and attempts began to be made to eliminate PCBs from the environment. However, the very properties that made PCBs desirable in the first place—chemical inertness and lack of flammability—made their destruction extremely difficult.

The most common method for disposal is to dilute PCBs with combustible organic materials and to incinerate them at extremely high temperatures (1100° C.).

This method has the significant drawback that incomplete combustion can lead to polychlorinated dibenzofurans which are known to be extremely toxic.

Many other methods have been developed most of which are based on the use of alkali metals (or their hydroxides), especially dispersions of sodium metal. A typical process using sodium is described in U.S. Pat. No. 4,340,471, Jul. 10, 1982. PCB-contaminated silicone-based or hydrocarbon oils have been treated with hydrocarbon dispersions of sodium (U.S. Pat. No. 4,379,746, Apr. 12, 1983). Sodium metal also has been used in the presence of an electron carrier (e.g., benzophenone, alkylbiphenyl) and an aprotic complexing solvent (e.g. tetrahydrofuran, dimethylformamide) in U.S. Pat. No. 4,377,471, Mar. 22, 1983. Japanese Patent No. 49082570 mentions the use of isopropanol with sodium and removes excess sodium with methanol. Carbon dioxide gas and water have been used to remove excess sodium (U.S. Pat. No. 4,416,767, Nov. 22, 1983).

Dehalogenation also has been carried out with alkali metal aromatic radical anion reagents e.g. sodium naphthalide, lithium anthracide—see U.S. Pat. No. 4,284,516, Aug. 18, 1981. This type of reagent has been used in the presence of ether-type solvents (U.S. Pat. No. 4,326,090, Apr. 20, 1982). The reaction may be quenched using carbon dioxide (U.S. Pat. No. 4,447,667, May 8, 1984).

Another type of dehalogenation has involved the use of hydrogen gas under pressure in the presence of a catalyst: the process requires elaborate equipment and is sensitive to impurities (U.S. Pat. No. 4,623,448, Nov. 18, 1986). Still another type of process has involved reaction with sulfur at high temperatures (U.S. Pat. No. 4,581,442, Apr. 8, 1986).

The PCB—contaminated silicone oils mentioned in prior art such as U.S. Pat. No. 4,379,746 are transformer oils, heat transfer fluids or lubricants based on polysilanes, and are distinct from hydrosiloxanes.

It would be desirable to provide such a dehalogenation process that would be more effective at room temperature, use relatively inexpensive reagents and equipment, and be relatively insensitive to impurities.

SUMMARY OF THE INVENTION

It has been found that hydrosiloxanes enhance the dehalogenation of halogenated aromatic materials when using alkali metal reactant.

The invention includes a process for dehalogenating aromatic halogenated compounds, comprising: reacting an alkali metal with halogenated aromatic material in the presence of a liquid hydrosiloxane, until substantially all of the halogen has reacted, leaving the aromatic moiety in non-halogenated form. Preferably a non-halogenated non-aqueous polar solvent or diluent is present during the reaction. The excess alkali metal can be reacted with added termination agent, and excess hydrosiloxane can be precipitated and the solids separated.

The invention includes a reagent mixture for dehalogenating halogenated aromatic material, comprising an alkali metal and a hydrosiloxane. The invention further includes a kit for dehalogenating halogenated aromatic material comprising: a container containing alkali metal, a container containing liquid hydrosiloxane, with the proviso that one container may contain both.

DETAILED DESCRIPTION

The starting material to be dehalogenated may be any halogenated aromatic compounds or mixtures containing such compounds. For example, the compounds may include halogenated benzenes, halogenated polyphenyls, and halogenated polynuclear aromatics. In most cases the compounds will be polychlorinated biphenyls alone or as mixtures with various oils such as hydrocarbons or silicone-based oils e.g. transformer oils, ballast oils, heat transfer fluids, or lubricants. Some chlorinated aromatic pesticides also may be treated.

The alkali metals suitably are lithium, sodium or potassium, with sodium being the most economical and most widely used. It is preferable to add the alkali metal in excess of the stoichiometric amount based on the halogen present, most preferably about a fivefold excess. The alkali metal may be added to the starting material as a suspension in a suitable inert liquid or alone. Preferably Li is added as a powder, K as small pieces, and Na as small pieces, shot or dispersion in paraffin, light oil or mineral spirits.

The hydrosiloxane should be a liquid miscible with the starting material. Preferably the hydrosiloxane will be a polyorganohydrosiloxane of relatively low molecular weight. Most preferred polyhydrosiloxanes are those of the formula

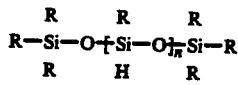

where R=lower alkyl of 1 to 4 carbon atoms and n=3-50.

Polymethylhydrosiloxanes of molecular weight about 1500-3000 are liquids of low viscosity and have been found very suitable. Normally the amount of polyhydrosiloxane added will be an excess (stoichiometric excess of available hydrogens from the polyhydrosiloxane relative to the chlorine sites) preferably at least about 20-fold excess. The polyhydrosiloxane should be present at the start of the reaction. If some water is present in the starting material, the polyhydrosiloxane may be added as a drying agent prior to addition of the alkali metal.

If desired, a non-halogenated, non-aqueous polar solvent or diluent may be present during the reaction. Such solvents or diluents are used to adjust the viscosity and facilitate contact of the alkali metal with the halogenated compounds. Suitable solvents or diluents include tetrahydrofuran, dioxane, dimethylformamide, dimethylsulfoxide, ethers such as ethyleneglycoldimethylether and diglyme, and mixtures thereof.

In the presence of the hydrosiloxane, the reaction will proceed readily at ambient temperatures and usually will be complete in about 10 to 24 hours. Slightly elevated temperatures (below the boiling point of solvents present) will shorten this time, but are not necessary.

When the dehalogenation reaction is substantially complete, a termination agent normally is added to destroy any excess alkali metal. Suitable termination agents include water, alkanols, glycols, phenols especially polyhydric phenols, carbon dioxide (gas or solid) and mixtures thereof. If desired, these agents can form a separate phase from the dehalogenated material if necessary with an immiscible organic species (such as liquid alkanes (pentane, hexane), petroleum ethers etc.) and can be separated. Some of these agents, particularly aqueous media, also serve as extractants to remove the alkali metal halide reaction product. The aqueous media form a separate phase which is readily removed, and since it contains no hazardous materials is suitable for disposal.

Excess hydrosiloxane can be precipitated and removed as a solid residue. Normally the termination agent also will precipitate excess hydrosiloxane. Preferred precipitants are alkanols (1-4C) and water. The precipitate may be separated by settling, filtration or centrifugation.

The polar solvent or diluent may be recovered from the dehalogenated material and recycled e.g. by distillation, membrane separation, preferential extraction etc. The residual organic material may be reused or safely incinerated.

A mixture of the hydrosiloxane and the alkali metal has been found to be quite stable (no loss of activity) if kept moisture free. This mixture constitutes a useful dehalogenation reagent which may used in various syntheses.

A kit which includes the liquid hydrosiloxane and alkali metal in the same or separate containers, is very useful for field decontaminations. The kit may also comprise a container containing the termination agent, a container containing the solvent or diluent and/or a container containing an aqueous medium for extraction of halide salt.

The following examples are illustrative and typical of the many tests which have been carried out.

EXAMPLE 1

A 100 mL three-necked round bottom flask equipped with a water cooled condenser, a septum, a gas inlet and a magnetic stirring bar was charged with a suspension of lithium powder (500 mg, 72.5 mmoles) in 25 mL of dry tetrahydrofuran which was stirred under an inert atmosphere of nitrogen or argon for 10 minutes. A solution of p-chlorobiphenyl (3.76 g., 20 mmoles) in 5 mL of dry tetrahydrofuran was added via syringe to the aforementioned suspension and the resulting mixture was then stirred for an additional 5 minutes. Polymethylhydrosiloxane of M.W. 2270 (5 g.) was added slowly, inducing an exothermic reaction. Upon completion of the addition the reaction mixture was stirred at ambient temperature for 16 hours to afford a homogeneous yellow coloured solution. The reaction mixture was cooled in an ice bath while methanol (ca 15 mL) was added dropwise. After addition of the alcohol the mixture was stirred in the ice bath for 3 hours to ensure the total destruction of the excess metal.

For analysis the resulting suspension was then concentrated under vacuum with the aid of a rotary evaporator (bath temperature: 40° C.) and the off-white solid thus obtained was partitioned between hexanes and water (ca. 100 mL), filtered, and the layers decanted in a separatory funnel. The aqueous phase was extracted with two 50 mL. portions of hexanes, and discarded. The combined organic extracts were dried over anhydrous magnesium sulfate and an aliquot was analyzed by gas chromatography (GC). This analysis indicated the complete conversion of the starting material into one new product, shown by comparison of its GC retention time with that of an authentic sample, gas chromatography-mass spectrometry (GC-MS) and its mixed melting point, to be biphenyl. The recovered yield of the latter product after removal of the solvent under reduced pressure and drying, was >99%.

Complex mixtures of polychlorinated biphenyls were purchased under the trademark Arochlor TM and samples were treated as follows.

EXAMPLE 2

Method A

A sample of Arochlor TM 1242 (100 mg., believed to contain about 42% by wt chlorine) was dechlorinated by treatment with 250 mg. of lithium powder and 3 g. of polymethylhydrosiloxane in the manner of Example 1. After workup as described above, using doubly deionized water, the aqueous phase was acidified with concentrated nitric acid and analyzed for Cl$^-$ ion by silver nitrate titration to a potentiometric endpoint. This analysis indicated that 100% of the chlorine from the PCB sample, corresponding to 42% of the total weight of the Arochlor TM 1242 was now in the aqueous phase. The organic phase, after the addition of a measured amount of decane as a standard for quantitation, was submitted to GC and GC-MS analyses, which indicated the complete disappearance of the original PCB components, the absence of any newly formed chlorine containing materials and the formation of biphenyl as the main product, accompanied by minor amounts (<10% of the total weight) of higher molecular weight oligomers (terphenyl, tetraphenyl). The total recovery of the organic material was better than 99%.

Method B

A 100 mg sample of Arochlor ™ 1242 was dechlorinated as described in Example 2, Method A, but using sodium (500 mg) as the metal. After workup as described above, analysis of organic phase indicated a level of dechlorinated comparable to that achieved with lithium metal.

Method C

A 100 mg sample of Arochlor ™ 1242 was dechlorinated as described in Example 2, Method A, but using sodium as the metal and dry toluene as the solvent. After the usual workup, analysis of the aqueous phase indicated the recovery of 90% of the chlorine originally present in the PCB sample as Cl$^-$ ion, while the organic phase contained no detectable levels of chlorinated materials. Up to 5% of the recovered organic material consisted of mixed biphenyl-solvent coupling products.

Method D

A 100 mg sample of Arochlor ™ 1242 was dechlorinated as described in Example 2, Method A, but employing a preformed suspension of lithium metal in polymethylhydrosiloxane which had been stored for 1 week prior to being used. The concentration of this suspension was comparable to that of the final reaction mixture described in Method A. The level of dechlorination attained was identical to that achieved by Method A.

Example 3

A 100 mg sample of Arochlor ™ 1254 (believed to contain about 54% by wt. chlorine) was dechlorinated as described in Example 2, Method A. After the usual workup, analysis indicated the complete absence of any chlorinated materials in the organic phase, which contained similar proportions of the same products obtained upon dechlorination of Arochlor ™ 1242.

Control dehalogenations with alkali metal as sole reactant were not complete at ambient temperatures even after several days (the products remained environmentally unacceptable). Test carried out in the presence of the solvent tetrahydrofuran (but in the absence of hydrosiloxane) were unsatisfactory since conversions were incomplete.

According to this invention significantly improved dehalogenations are achieved at ambient temperatures. This method using hydrosiloxanes leads to the destruction of PCB's to the point where they can no longer be detected by GC.

We claim:

1. A process for dehalogenating aromatic halogenated compounds, comprising: reacting an alkali metal with halogenated aromatic material in the presence of a liquid hydrosiloxane, until substantially all of the halogen has reacted, leaving the aromatic moiety in non-halogenated form, and the available hydrogen groups from the hydrosiloxane being at least as numerous as the halogen groups present.

2. The process of claim 1 wherein the hydrosiloxane is a polyalkylhydrosiloxane of the formula:

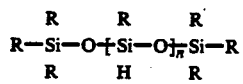

where
R=lower alkyl of 1–4 C atoms,
and
n=3–50.

3. The process of claim 1 wherein a non-halogenated non-aqueous polar solvent or diluent is present during the reaction.

4. The process of claim 1 wherein the alkali metal is lithium or sodium, and is present in excess of stoichiometric amounts relative to the halogen.

5. The process of claim 4, wherein after the reaction excess alkali metal is removed by the addition of a termination agent selected from the group consisting of water, alkanols, glycols, phenols, carbon dioxide, and mixtures thereof.

6. The process of claim 1 wherein after the reaction alkali metal halide reaction product is separated by extraction with an aqueous medium.

7. The process of claim 3 wherein after the reaction alkali metal halide reaction product is separated by extraction with an aqueous medium substantially insoluble in said solvent or diluent.

8. The process of claim 1 wherein the halogenated aromatic material comprises a chlorinated benzene, chlorinated polyphenyl, or a chlorinated polynuclear aromatic compound.

9. The process of claim 1 wherein water is present in the halogenated starting material and the hydrosiloxane is added prior to the alkali metal, to remove the water.

10. The process of claim 5 wherein after the reaction has been terminated, precipitated excess hydrosiloxane is removed.

11. The process of claim 3 wherein the solvent is selected from the group consisting of tetrahydrofuran and toluene.

12. The process of claim 3 wherein the solvent is separated after the reaction and recycled.

13. The process of claim 7 wherein, after the extraction, the solvent is separated and recycled.

14. The process of claim 1 wherein the halogen is chlorine or bromine.

* * * * *